United States Patent [19]

Seifert et al.

[11] 4,430,453
[45] Feb. 7, 1984

[54] POLYURETHANE FOAMS SUITABLE FOR HIGH FREQUENCY WELDING AND PROCESS FOR PRODUCING THE SAME

[75] Inventors: Peter Seifert, Berg.-Gladbach; Peter Haas, Haan, both of Fed. Rep. of Germany

[73] Assignee: Bayer Aktiengesellschaft, Leverkusen, Fed. Rep. of Germany

[21] Appl. No.: 436,471

[22] Filed: Oct. 25, 1982

[30] Foreign Application Priority Data

Nov. 4, 1981 [DE] Fed. Rep. of Germany ....... 3143706

[51] Int. Cl.$^3$ ............................................. C08G 18/14
[52] U.S. Cl. ..................................... 521/107; 521/108
[58] Field of Search ................................ 521/107, 108

[56] References Cited

U.S. PATENT DOCUMENTS

| | | | |
|---|---|---|---|
| 3,933,697 | 1/1976 | Fujii et al. | 260/2.5 A |
| 4,061,605 | 12/1977 | Simon | 521/108 |
| 4,129,693 | 12/1978 | Cenker et al. | 521/106 |
| 4,146,509 | 3/1979 | Markusch et al. | 521/107 |
| 4,165,411 | 8/1979 | Marans et al. | 521/107 |
| 4,208,485 | 6/1980 | Nahta | 521/107 |
| 4,235,976 | 11/1980 | Haas et al. | 521/107 |
| 4,328,321 | 5/1982 | Haas et al. | 521/108 |
| 4,371,630 | 2/1983 | Konig et al. | 521/173 |

FOREIGN PATENT DOCUMENTS 328749  4/1976  Austria .

OTHER PUBLICATIONS

Chemical Abstracts, Band 77, No. 8, Aug. 21, 1972, Seite 55, No. 49530b, Columbus, Ohio.

*Primary Examiner*—Maurice J. Welsh
*Attorney, Agent, or Firm*—Gene Harsh; Joseph C. Gil

[57] ABSTRACT

This invention relates to polyurethane foams capable of being welded by high frequency welding and a process for producing the same, characterized by the addition of certain ammonium salts of acids containing phosphorus to the starting components for the polyurethane foam in order that the polyurethane starting materials and the polyurethanes contain from 0.1 to 10%, by weight, of ammonium salts of phosphorus-containing acids. Phosphorus-containing ammonium salts which are available in the liquid form and completely soluble in polyols are particularly suitable with salts of phosphoric acid mono- and dibutyl esters, dialkyl phosphinic acids, alkyl phosphonic acids and alkyl phosphonic acid monomethyl esters being preferred. The addition of these acids significantly increases the dielectric loss factor of thermoplastic polyurethane foams and, therefore, also considerably increases their capacity for being welded by high frequency welding.

9 Claims, No Drawings

POLYURETHANE FOAMS SUITABLE FOR HIGH FREQUENCY WELDING AND PROCESS FOR PRODUCING THE SAME

The present invention relates to polyurethane foams suitable for high frequency welding and to a process for producing the same, characterized by the addition of certain ammonium salts of acids containing phosphorus to the starting components used for producing the polyurethane foams, in order that the polyurethane starting materials contain from 0.1 to 10% by weight of ammonium salts of these phosphoric acids.

BACKGROUND OF THE INVENTION

The suitability of a polymer material for being welded by high frequency welding is determined by two criteria:

1. Thermoplasticity; i.e., the material must change from the solid to the liquid state at a temperature below its decomposition temperature, the temperature for the change of state being preferably preceded by a softening temperature range.
2. Dielectric loss factor; i.e., the capacity to absorb energy from a high frequency electric alternating field. This characteristic is a constant of the material.

Foamed materials are generally welded, not to themselves, but to textiles or foils or pressed boards. The dielectric loss factor of the composition material is, of course, strongly influenced by these other materials and the effect of these other materials frequently overrides that of the polyurethane foam. However, a high dielectric loss factor is, nevertheless, still desirable in foams, since it enables them to be welded to any materials, including those which do not themselves have a dielectric loss factor (e.g., textiles of pure polyethylene terephthalate fibers).

Among the usual homogeneously-foamed materials, PVC foam has hitherto been the only one which amply fulfills both the conditions of thermoplasticity and of dielectric loss factor. Its high cost, high weight and poor mechanical properties, however, have prevented it from being widely used. Other materials available for high frequency welding include thermoplast-modified polyester polyurethane foams.

Polyurethane foams may be rendered suitable for high frequency welding by, for example, stitching the foam with thermoplastic fibers which have a dielectric loss factor, or by spraying thermoplastic high frequency-active powder over the foam. These methods have both practical and economic disadvantages inherent in the systems, however. Stitching requires the foam to be perforated and the stitched surface cannot be covered with surface layers by flame laminating. Spraying powder over the foam means that some powder may trickle out of the product and soil the machinery or the surface of the foam. Both these methods are expensive.

Incorporation of thermoplastic powder into the stream of raw material during the foaming process is a more efficient method of rendering the polyurethane foam suitable for high frequency welding, but the quantity which may be added in this manner is limited by the resulting sharp increase in the viscosity of the polyester polyol which is already highly viscous. Moreover, uniform distribution of the solids in the foam is difficult and the unavoidable inclusion of gas also causes problems.

Considerable progress in the production of foams capable of being welded by high frequency welding was provided by the development of polyurethane solutions in polyether polyols as described in German Offenlegungsschriften 3,008,590 and 2,937,509. Such foams may be produced as completely homogeneous products and are eminently suitable for welding with any high frequency active material. Problems still occur, however, when these foams are to be welded with surface layers which have no dielectric loss factor (e.g., textiles of pure polyester fibers), since the foam alone absorbs too little energy due to its relatively low dielectric loss factor. This low absorption of energy by the foam results in a greatly prolonged welding time or very high energy requirement, both of which increases the risk of burning the material. Although the production of high frequency weldable polyether polyurethane foams according to the teaching of these references provides considerable improvements compared with standard polyether polyurethane foams, experience has indicated that there is still considerable room for improvement.

It has now surprisingly been found that the dielectric loss factor of polyurethane foams, including those foams which may be produced according to German Offenlegungsschriften Nos. 3,008,590 and 2,937,509, may be significantly increased by the addition of the ammonium salts of phosphorus-containing acids according to the invention.

As shown by the Examples, a considerably-improved capacity for high frequency welding is achieved, even with materials which are not themselves capable of being heated by high frequency. Thus, for example, this technique may readily be employed even for welding textiles which do not have a dielectric loss factor necessitating that the entire loss factor be provided by the foam. The increase in loss factor was surprisingly achieved by introducing ammonium salts of phosphorus-containing acids into the polyurethane foams.

DESCRIPTION OF THE INVENTION

The present invention, therefore, relates to a process for the production of polyurethane foams which are easily welded by high frequency, by the reaction of relatively high molecular weight compounds having molecular weights of from 400 to 10,000 containing at least two isocyanate-reactive hydrogen atoms, with polyisocyanates, and optionally, chain-lengthening agents having molecular weights of from 32 to 399, in the presence of catalysts, optionally, in the presence of foam stabilizers, water and/or organic blowing agents, and other auxiliary agents and additives, characterized in that ammonium salts of phosphorus-containing acids are added in quantities of from 0.1 to 10% by weight, based on the total weight of the reaction mixture. The preferred ammonium salts of phosphorus-containing acids, correspond to the formula

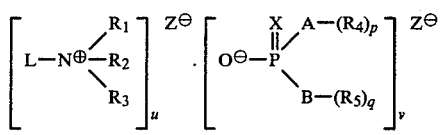

wherein
L represents hydrogen and/or a $C_1$ to $C_6$ alkyl;
$R_1$, $R_2$, and $R_3$ are the same or different and represent a member selected from the group consisting of (i) hydrogen,
(ii) linear or branched chain hydroxyalkylene groups with up to 10 C-atoms, preferably $-(CH_2)_e-OH$,
(iii) linear or branched chain alkyl and cycloalkyl groups with up to 10 C-atoms, which may contain $-O-$ or $-N-$alkyl-groups; preferably $-(CH_2)_e-H$,
(iv)

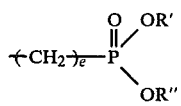

where R' and R" are the same or different and represent a $C_1$ to $C_{10}$ alkyl or hydroxyalkyl,
(v)

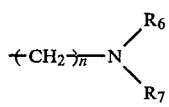

where $R_6$ and $R_7$ are the same or different and represent a linear or branched $C_1$ to $C_6$ alkyl (preferably methyl or ethyl),
(vi)

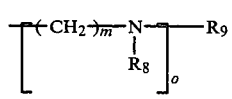

where $R_8$ and $R_9$ are the same or different and represent a linear or branched $C_1$ to $C_6$ alkyl (preferably methyl or ethyl),
(vii)

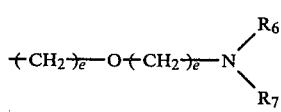

where $R_6$ and $R_7$ are as defined above, and
(viii)

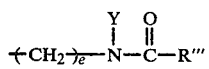

where R''' represents hydrogen or a $C_1$ to $C_6$ alkyl, and where Y represents any one of the radicals noted under (i) through (vii) above; and further wherein
e represents an integer of from 1 to 10,
n represents an integer of from 2 to 10,
m represents an integer of from 2 to 10,
o represents an integer of from 2 to 6,
$Z^\oplus$ is the charge number of the cation, may be equal to or less than the total number of nitrogen atoms and is preferably 1 or 2, and
u denotes the number of cations (preferably one or two) that may be present depending on the charge number $Z^\oplus$, such that $uZ^\oplus = vZ^\ominus$ (it is preferable that $uZ^\oplus$ equal one or two);
X represents an oxygen or sulfur atom;

A and B are the same or different and represent a member selected from the group consisting of
(i) $-CH_2-$
(ii) an oxygen or sulfur atom, and
(iii) an oxygen ($O^\ominus$) or sulfur ($S^\ominus$) ion;
p and q are either 0 or 1, and when A and/or B represents an oxygen or sulfur ion, the corresponding p or q must be zero;
$Z^\ominus$ is the charge number of the anion,
v represents the number of anions present, being an integer of 1 to 3, (preferably 1 to 2), such that $vZ^\ominus = uZ^\oplus$;
and
$R_4$ and $R_5$ may be the same or different and represent hydrogen or a $C_1$ to $C_{10}$ alkyl or cycloalkyl.

The salts are added to the starting components for the foam, preferably dissolved in one or more of the starting components for producing the foam, in quantities of from 0.1 to 10% by weight, based on the total weight of the mixture.

It is preferred to employ a process in which the ammonium salts of the phosphorus-containing acids are dissolved in the compounds containing at least two isocyanate-reactive hydrogen atoms. It is less preferred to dissolve the ammonium salts in the polyisocyanates.

If, for example, the cation is monovalent (1 $N^\oplus$), then the anion can also be monovalent. If the cation is divalent (e.g., 2 $N^\oplus$), then the anion must also be divalent (e.g., $-A$ in the above formula represents an oxygen ion), or two monovalent anions must be present. Similarly, two monovalent cations may be present with a divalent anion.

The invention also relates to polyurethane foams suitable for high frequency welding which are obtained from relatively high molecular weight polyhydroxyl compounds in the molecular weight range of from 400 to 10,000, polyisocyanates, optionally chain-lengthening agents with molecular weights of from 18 to 399, catalysts, optionally foam stabilizers, water and/or organic blowing agents, and auxiliary agents and additives, characterized in that they contain from 0.1 to 10% by weight of ammonium salts of phosphorus-containing acids, preferably corresponding to the above-noted formula.

Particularly suitable additives according to the invention for increasing the capacity of the polyurethane foams for high frequency welding, particularly of polyurethane foams containing polyethers, are those phosphorus-containing salts which are present in a liquid form and are completely soluble in polyols.

Preferred phosphorus-containing acids from which these additives may be produced, include mono- and dialkyl phosphoric and phosphinic acids, alkyl phosphonic acids and their monoalkyl esters. It is particularly preferred according to the invention to use the salts of phosphoric acid dibutyl ester and of phosphoric acid di-(2-ethylhexyl)-ester.

The amine components used to form the ammonium salts are preferably the relatively non-odorous amines described in German Offenlegungschriften Nos. 2,624,527; 2,732,292; 2,909,482; 3,027,796 and 3,046,905.

Examples of such amine components include:

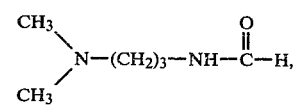

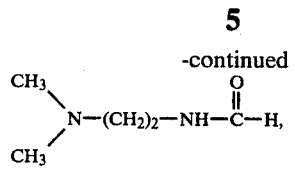
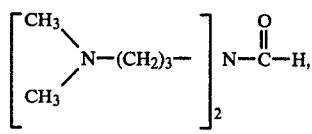
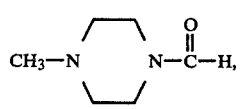
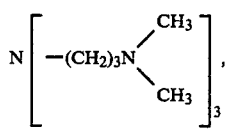
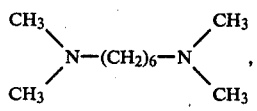
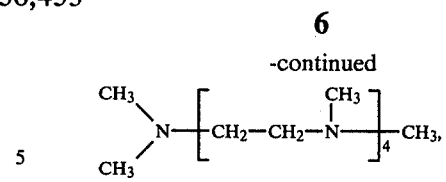
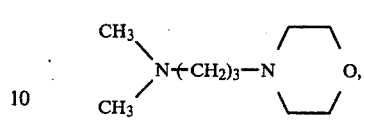
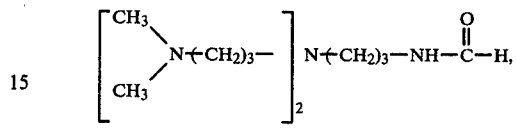
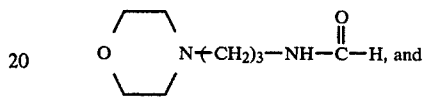
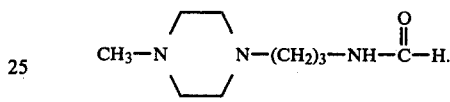
The following are specific examples of the class of salts according to the invention for increasing the dielectric loss factor in high frequency welding of polyurethane foams:
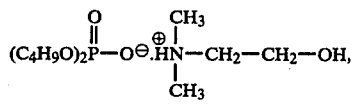
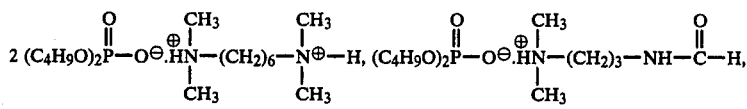
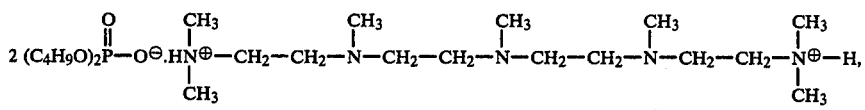
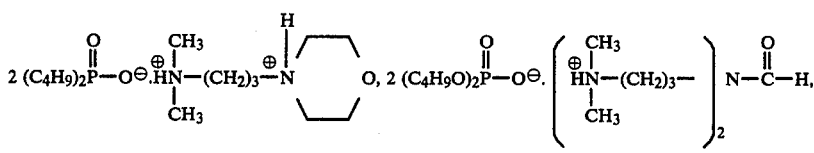
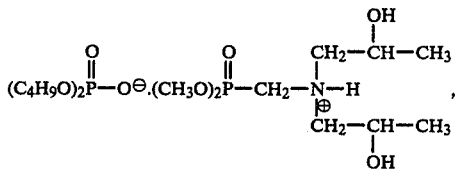
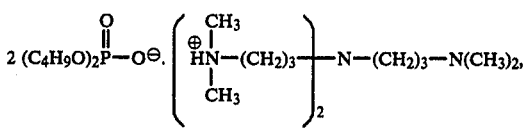

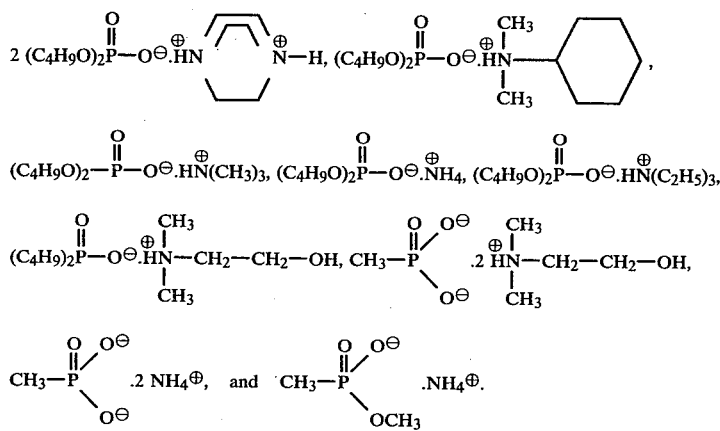

The additives according to the invention include those prepared by partially or completely neutralizing the phosphorus-containing acids, e.g., phosphoric acid dibutyl ester, phosphoric acid bis-(2-ethylhexyl ester), dibutyl phosphinic acid, methyl phosphonic acid, or methyl phosphonic acid monomethyl esters, with basic nitrogen-containing compounds. Suitable nitrogen-containing compounds include, for example, tetramethyl hexamethylene diamine, heptamethyl tetraethylene pentamine, dimethylaminopropyl formamide, bis-(dimethylaminopropyl)-formamide, dimethylaminopropyl morpholine, tris-(dimethylamino-n-propyl)-amine, ethanolamine, diethanolamine, dimethylaminoethanol, methyldiethanolamine, triethylamine, dimethyl cyclohexylamine, pentamethyl diethylene triamine, dimethylaminopropyl-methyl-piperazine, piperazine, triethylene diamine, diisopropylamine, hexamethylene diamine, bis-(2-hydroxyethyl)-aminomethyl-phosphonic acid dimethyl ester, adipic acid-bis-(2-dimethylaminoethyl ester), 1,8-diazabicyclo-(5,4,0)-undec-7-ene, 1,5-diazabicyclo-(5,4,0)-non-5-ene, orthoformic acid-tris-dimethylaminoethyl ester, bis-(dimethylaminoethyl)-ether, and the like.

The amines which have been partly or completely protonated with phosphorus-containing acids are used in the polyurethane formulation in quantities of from 0.1 to 10%, preferably 1 to 5% (based on the total weight) and are preferably incorporated in the polyol stream. The products to be used according to the invention are, for the most part, liquid to viscous substances which, for ease of handling, may be worked up as aqueous solutions or solutions in higher functional alcohols.

The polyurethane foams of the invention may be prepared from known starting components.

These include relatively high molecular weight compounds, generally with molecular weights of from 400 to 10,000, containing at least two isocyanate reactive hydrogen atoms. Apart from compounds containing amino groups, thiol groups or carboxyl groups, these include, in particular, compounds containing hydroxyl groups, preferably 2 to 8 hydroxyl groups, and especially those with molecular weights of from 1000 to 6000, preferably of from 2000 to 4000. Examples of such compounds include polyesters, polyethers, polythioethers, polyacetals, polycarbonates, polylactones and polyester amides having at least 2, generally 2 to 8, preferably 2 to 4 hydroxyl groups, such as those commonly used for the preparation of both homogeneous and cellular polyurethanes; such compounds have been described in detail, e.g., in German Offenlegungsschrift No. 2,832,253, pages 11–18.

For optimum results, it is also preferred to use the modified polyhydroxyl compounds as described in German Offenlegungsschriften Nos. 3,008,590 and 2,937,509.

The polyisocyanate components may be aliphatic, cycloaliphatic, araliphatic, aromatic or heterocyclic polyisocyanates, such as those described, for example, by W. Siefken, in Justus Liebigs Annalen der Chemie, 362, pages 75–136. Such polyisocyanates correspond, for example, to the formula:

$$Q(NCO)_n$$

wherein n is a number from 2 to 4, preferably 2, and

Q denotes an aliphatic hydrocarbon group having 2 to 18, preferably 6 to 10 carbon atoms, a cycloaliphatic hydrocarbon group having 4 to 15, preferably 5 to 10 carbon atoms, an aromatic hydrocarbon group having 6 to 15, preferably 6 to 13, carbon atoms or an araliphatic hydrocarbon group having 8 to 15, preferably 8 to 13 carbon atoms, e.g., the polyisocyanates described in German Offenlegungsschrift No. 2,832,253, pages 10–11.

As a general rule, it is particularly preferred to use commercially available polyisocyanates such as 2,4- and 2,6-tolylene diisocyanate and mixtures of these isomers ("TDI"), polyphenyl-polymethylene polyisocyanates which may be prepared by aniline-formaldehyde condensation followed by phosgenation ("crude MDI") and polyisocyanates containing carbodiimide groups, urethane groups, allophanate groups, isocyanurate groups, urea groups or biuret groups ("modified polyisocyanates") and, in particular, those modified polyisocyanates which are derived from 2,4- and/or 2,6-tolylene diisocyanate or from 4,4'- and/or 2,4'-diphenylmethane diisocyanate.

The starting components may also include chain-lengthening agents and/or cross-linking agents with molecular weights of from 32 to 399 containing at least two isocyanate reactive hydrogen atoms. These agents also include compounds containing hydroxyl groups and/or amino groups and/or thiol groups and/or carboxyl groups, preferably hydroxyl groups and/or amino groups, and may be used as chain-lengthening agents or cross-linking agents. These compounds generally have from 2 to 8, preferably 2 to 4, isocyanate reactive hydrogen atoms. Examples of such agents are described in German Offenlegungsschrift No. 2,832,253, pages 19-20.

Additional auxiliary agents and additives which may be used include: water and/or readily volatile inorganic or organic substances as blowing agents; catalysts; surface active additives, such as emulsifiers and foam stabilizers; reaction retarders, e.g., substances which are acid in reaction, such as hydrochloric acid or organic acid halides; cell regulators, such as paraffins or fatty alcohols or dimethyl polysiloxanes; pigments; dyes; and flame retarding agents, e.g., tris-chloroethyl phosphate, tricresyl phosphate or ammonium phosphate and polyphosphate; stabilizers against ageing and weathering; plasticizers; fungistatic and bacteriostatic substances; and fillers, such as barium sulfate, kieselguhr, carbon black or whiting. Many of these optionally-used auxiliary agents and additives are generally known and have been described, for example, in German Offenlegungsschrift No. 2,732,292, pages 21-24. Other examples of surface active additives and foam stabilizers optionally used according to the invention, as well as cell regulators, reaction retarders, stabilizers, flame retardants, plasticizers, dyes, fillers and fungistatic and bacteriostatic substances, as well as details concerning their use and mode of action, may be found in Kunststoff Handbuch, Vol. VII, published by Vieweg and Höchtlen, Carl Hanser Verlag, Munich, 1966, e.g., on pages 103-113.

To carry out the process according to the invention the reactants, one or more of which contain the ammonium salts of phosphoric acids, are reacted together by the known one-shot process, the prepolymer process or the semi-prepolymer process, frequently using mechanical devices such as those described in U.S. Pat. No. 2,764,565. Details concerning processing apparatus suitable for use according to the invention are given in Kunststoff Handbuch, Vol. VII, published by Vieweg and Höchtlen, Carl Hanser Verlag, Munich, 1966, e.g., pages 121-205.

In the process according to the invention for producing polyurethane foam, foaming is preferably carried out in closed molds. The reaction mixture is introduced into a mold, which may be made of metal, e.g., aluminum, or of a polymer material, e.g., an epoxide resin and it foams inside this mold to form the shaped product. Foaming in the mold may be carried out to produce a product having a cellular structure on its surface or it may be carried out in such a manner that a product with non-cellular skin and a cellular core are obtained. According to the invention, the desired result may be obtained by introducing just sufficient foamable reaction mixture to fill the mold with foam or by introducing a large quantity of reaction mixture than is necessary to fill the interior of the mold with foam. The latter method is known as "overcharging", and has been disclosed, for example, in U.S. Pat. Nos. 3,178,490 and 3,182,104.

So called "external mold release agents", such as silicone oils, are frequently used in the preferred method of foaming in molds, but so called "internal mold release agents" may also be used, optionally together with external mold release agents as disclosed, for example, in German Offenlegungsschriften Nos. 2,121,670 and 2,307,589.

According to the invention, it is preferred to produce cold setting molded foams which have been foamed up in a cold mold (see British Pat. No. 1,162,517 and German Offenlegungsschrift 2,153,086). The foams may, of course, also be produced by block foaming or by the known laminator process.

Polyether urethane foams which have an increased dielectric loss factor due to the presence of the additives according to the invention may be used in, for example, polyurethane upholstery for motor car seats covered with textiles or foil, door panelling, handles, interior fittings for motor cars, and various sandwich materials or laminates used in the leather goods industry, shoe industry and furniture industry.

EXAMPLES (A) Preparation of ammonium salts of phosphorus-containing acids:

Example 1

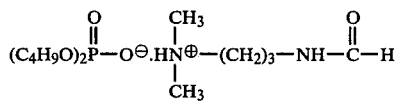

130 g (1 mol) of dimethylaminopropyl formamide are added dropwise to 210 g (1 mol) of dibutyl phosphate at 10° C. with cooling. The viscous reaction product, which has a viscosity of $n_D^{20} = 1.4615$, slowly crystallizes. It melts at 28° C. and may be kept liquid at high concentrations in aqueous solution, n=1.4428 (80% solution in water).

Example 2

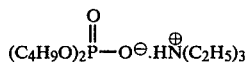

Prepared by the method of Example 1 from 210 g (1 mol) of dibutyl phosphate and 101 g (1 mol) of triethylamine; product viscosity, $n_D^{20} = 1.4440$.

Example 3

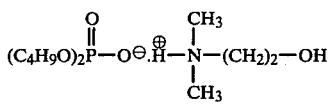

Prepared by the method of Example 1 from 210 g (1 mol) of dibutyl phosphate and 89 g (1 mol) of dimethyl ethanolamine; product viscosity, $n_D^{20} = 1.4750$.

Example 4

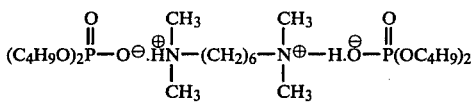

Prepared by the method of Example 1 from 420 g (2 mol) of dibutyl phosphate and 172 g (1 mol) of tetramethyl hexamethylene diamine; product viscosity, $n_D^{20} = 1.4549$.

Example 5

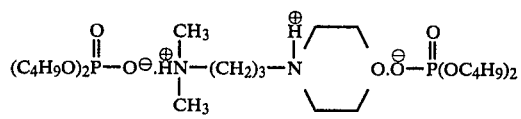

Prepared by the method of Example 1 from 210 g (1 mol) of dibutyl phosphate and 86 g (0.5 mol) of dimethylaminopropyl morpholine; product viscosity, $n_D^{20}=1.4595$.

Example 6

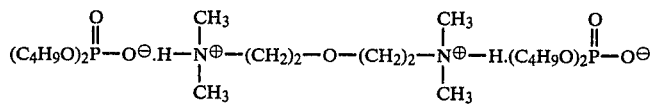

Prepared by the method of Example 1 from 210 g (1 mol) of dibutyl phosphate and 80 g (0.5 mol) of bis-(dimethylaminoethyl)-ether.

Example 7

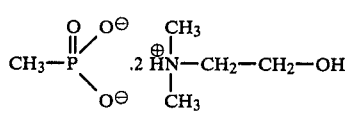

72.5 g (0.8 mol) of dimethylethanolamine are added dropwise to 39 g (0.40 mol of methyl phosphonic acid in 100 ml of methanol with cooling, and the mixture is then concentrated by evaporation. A quantitative yield of a yellow oil results.

Example 8

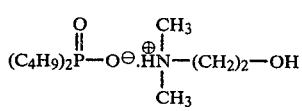

15.5 g (0.174 mol) of dimethylaminoethanol are added dropwise to 31 g (0.174 mol) of dibutyl phosphinic acid with cooling. A quantitative yield of a yellowish oil results.

Example 9

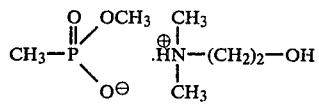

40 g (0.45 mol) of dimethylethanolamine are added dropwise to 54 g (0.455 mol) of methyl phosphonic acid monomethyl ester with cooling.

Example 10

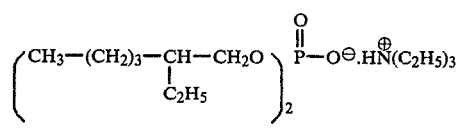

Prepared from 322 g (1 mol) of phosphoric acid-di-(2-ethylhexyl ester) and 101 g (1 mol) of triethylamine by the method of Example 1.

Example 11

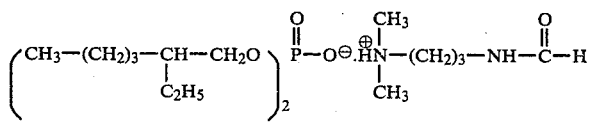

Prepared from 322 g (1 mol) of phosphoric acid-di-(2-ethylhexyl ester) and 130 g (1 mol) of dimethylaminopropyl formamide by the method of Example 1.

Example 12

Prepared from 210 g (1 mol) of dibutyl phosphate and 119 g (1 mol) of methyldiethanolamine by the method of Example 1; product viscosity, $n_D^{20}=1.4582$.

Example 13

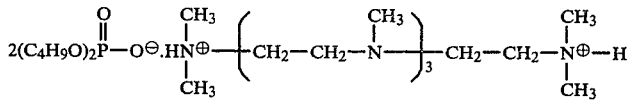

Prepared from 210 g (1 mol) of dibutyl phosphate and 140 g (0.5 mol) of heptamethyl tetraethylene pentamine according to the method of Example 1.

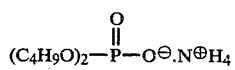

Example 14

Ammonia is passed over 105 g (0.5 mol) of dibutyl phosphate in 100 ml of toluene at 10° C. The precipitate is suction-filtered, washed with toluene and dried. Yield: 113 g of a colorless powder with a melting point of 133°–134° C. that is completely soluble in water.

| Analysis for C$_8$H$_{22}$NO$_4$P (227) | | | | |
| --- | --- | --- | --- | --- |
| Calculated | N | 6.1 | P | 13.6 |
| Actual | N | 6.0 | P | 13.4 |

(B) Examples of the production of foam using these additives:

Preparation of the polyurethane flexible foams with increased dielectric loss factor which may be welded by high frequency welding was carried out on a continuously-operating high pressure block foaming machine (manufactured by Hennecke, Birlinghoven, Siegkreis) or by the manual foaming process. In the manual foaming process, the polyols were mixed with stabilizer, activators and water and after addition of the isocyanate, the mixture was again vigorously mixed and the foaming mixture was poured into a paper packet and reheated at 100° C. for 30 minutes. The liquid ammonium salts, or ammonium salts which have been liquefied by the addition of suitable solvents, were either mixed with the polyol (manual mixing process) or fed into the mixing head of the foaming machine. The formulation is marked "H" or "M" according to whether the manual mixing process or the machine foaming process has been employed.

To test the suitability for high frequency welding, two foam panels, each 1 cm in thickness, are welded until the foam is completely plasticized by heat at the seam.

For welding foams to textiles, a sandwich construction was used, consisting of 0.8 cm of foam with polyamide Charmeuse weighing 60 g/m$^2$ on its under surface and Trevira ® crushed velour (unit weight: 320 g/m$^2$) on its upper surface.

The electrodes were insulated by means of a Teflon glass silk lining which is inert to high frequency so that the capacity for welding depends only on the thermoplasticity and dielectric loss factor of the foam.

The high frequency welding instrument used was a high frequency generator, G 4000 SD, manufactured by Kiefel, Freilassing (Power 4.3 Kw, frequency 27, 12 MHz).

The following conditions were observed:

|  | Foam/foam | Foam/textile |
| --- | --- | --- |
| Electrode surface | 1.44 ± 10 cm | 1.44 ± 10 cm |
| Pressure | 250 kp | 250 kp |
| Welding tension | 900 volt | 1000 volt |
| Welding time | variable | variable |

The isocyanates used:

| TDI 80 | tolylene diisocyanate (80% 2,4- and 20% 2,6-isomers) |
| --- | --- |
| TDI 65 | tolylene diisocyanate (65% 2,4- and 35% 2,6-isomers) |

Polyol used:

Mixture of 50% of a 20% solution (prepared according to Example A-5 of German Offenlegungsschrift No. 3,008,590) of a polyurethane of neopentyl glycol and TDI 80 in a linear polypropylene glycol polyether having an OH number 112
and
50% of a polyol started by the addition of a mixture of propylene oxide and ethylene oxide (90:10) to a mixture of glycerol and propylene glycol-(1,2) (predominantly glycerol) having the OH number 45.

The overall OH number of the polyol mixture is 71.

TABLE 1

Preparation of PU elastic foams capable of high frequency welding using various quantities of the additive compound according to Example 3 (Examples 15–18)

|  | 15(M) | 16(M) | 17(M) | 18(M) |
| --- | --- | --- | --- | --- |
| Starting Components (parts by weight) | | | | |
| Polyol | 100 | 100 | 100 | 100 |
| Water | 2.5 | 2.5 | 2.5 | 2.5 |
| Commercial elastic foam stabilizer (polyalkylene glycol-polysiloxane copolymer)+ | 0.8 | 0.8 | 0.8 | 0.8 |
| Dimethyl ethanolamine | 0.6 | 0.6 | 0.4 | 0.5 |
| Commercial amine activator (PS 207 of Bayer AG) | 0.15 | 0.15 | 0.15 | 0.15 |
| Tin-(II)-octoate | 0.15 | 0.1 | 0.1 | 0.08 |
| TDI 80 | 19.5 | 19.5 | — | — |
| TDI 65 | 19.5 | 19.5 | 39.0 | 39.0 |
| Isocyanate index | 106 | 106 | 106 | 106 |
| Additive according to Example 3 | — | 1 | 2 | 4 |
| Physical properties of the resulting foam | | | | |
| Density (kg/cm$^3$) | 36 | 36 | 35 | 36 |
| Tensile strength (kPa) | 125 | 135 | 140 | 120 |
| Elongation at break (%) | 200 | 210 | 280 | 270 |
| Compression resistance at 40% (kPa) | 4.2 | 3.9 | 3.5 | 3.2 |
| Pressure deformation residue at 90% (%) | 4.8 | 5.2 | 10.3 | 87 |
| Welding time foam/foam (sec) | 7 | 5 | 4 | 3 |
| Welding time foam/polyester textile | 10 | 6 | 5 | 4 |

+Stabilisator OS-22 of BAYER AG - D-5090 Leverkusen

The foams obtained by the process indicated in Table 1 are open-celled and may easily be flame-laminated to textiles and surface foils. The welding seams obtained are well marked (characteristic of foams welded to polyester textiles) and the foam is fused to a thin film at those seams. There are no burn marks and the welding seams cannot be separated without tearing the foam laterally to the seam. The resistance to separation by tearing of a 5 cm wide strip (force of adherence between upper material and foam) is about 60 N.

These examples illustrate that the capacity for high frequency welding is considerably improved by the additive. The welding time is also considerably reduced and hence, the time of the production cycle is reduced to an acceptable level (comparing the times actually experienced with the "normal" welding time for foam/foam of more than 20 seconds). Similarly, advantageous results are achieved when additives according to the invention are used for foams in the process characterized in Tables 2 and 3.

TABLE 2

Preparation of flexible foams suitable for high frequency welding using various ammonium salts of dibutyl phosphoric acid (Examples 19–26)

| | 19(M) | 20(M) | 21(M) | 22(M) | 23(M) | 24(M) | 25(M) | 26(M) |
|---|---|---|---|---|---|---|---|---|
| Starting Components (parts by weight) | | | | | | | | |
| Polyol | 100 | 100 | 100 | 100 | 100 | 100 | 100 | 100 |
| Water | 2.5 | 2.5 | 2.2 | 2.5 | 2.5 | 2.5 | 2.5 | 2.5 |
| Commercial flexible foam stabilizer (polyalkylene glycol-polysiloxane copolymer)-OS-22 - Bayer AG. | 0.8 | 0.8 | 0.8 | 0.8 | 0.8 | 0.8 | 0.8 | 0.8 |
| Dimethyl ethanolamine | 0.6 | 0.5 | 0.6 | 0.6 | 0.6 | 0.6 | 0.6 | 0.5 |
| Commercial amine activator (PS 207 of Bayer AG) | 0.15 | 0.15 | 0.15 | 0.15 | 0.15 | 0.15 | 0.15 | 0.5 |
| Tin-(II)-octoate | 0.15 | 0.1 | 0.1 | 0.08 | 0.05 | 0.12 | 0.09 | 0.05 |
| TDI 80 | 19.5 | 9.75 | 19.5 | 9.75 | 19.5 | % | 19.5 | % |
| TDI 65 | 19.5 | 29.5 | 19.5 | 29.25 | 19.5 | 39.0 | 19.5 | 39.0 |
| Isocyanate index | 106 | 106 | 106 | 106 | 106 | 106 | 106 | 106 |
| Additive according to Example 4 | — | 1.5 | — | %— | — | — | — | — |
| Additive according to Example 1 | — | — | 1.5 | %— | — | — | — | — |
| Additive according to Example 13 | — | — | — | 1.5 | — | — | — | — |
| Additive according to Example 5 | — | — | — | %— | 1.5 | — | — | — |
| Additive according to Example 6 | — | — | — | %— | — | 1.5 | — | — |
| Additive according to Example 10 | — | — | — | %— | — | — | 1.5 | — |
| Additive according to Example 14 | — | — | — | %— | — | — | — | 1.5 |
| Physical properties | | | | | | | | |
| Density (kg/cm³) | 36 | 34 | 37 | 36 | 35 | 34 | 34 | 34 |
| Tensile strength (kPa) | 125 | 125 | 145 | 130 | 115 | 140 | 145 | 115 |
| Elongation at break (%) | 200 | 266 | 350 | 290 | 250 | 350 | 400 | 380 |
| Compression resistance at 40% (kPa) | 4.2 | 2.8 | 3.3 | 2.3 | 2.8 | 2.9 | 2.7 | 2.1 |
| Pressure deformation residue at 90% (%) | 4.8 | 8.1 | 7.9 | 11.0 | 14.0 | tacky | 14.0 | tacky |
| Welding time foam/foam (sec) | 7 | 4 | 3.5 | 3.5 | 4 | 3 | 2.5 | 3 |

TABLE 3

Preparation of flexible foams suitable for high frequency welding using various ammonium salts of phosphonic and phosphonic acids (Examples 27–29)

| | 27(H) | 28(H) | 29(H) |
|---|---|---|---|
| Starting components (parts by weight) | | | |
| Polyol | 100 | 100 | 100 |
| Water | 2.5 | 2.5 | 2.5 |
| Commercial flexible foam stabilizer OS-22 (Bayer AG) (polyalkylene glycol-polysiloxane polymer) | 0.8 | 0.8 | 0.8 |
| Dimethyl ethanolamine | 0.15 | 1.0 | 0.15 |
| Commercial amine activator (PS 207 of Bayer AG) | 0.15 | 1.5 | 0.6 |
| Tin-(II)-octoate | 0.5 | 0.15 | 0.1 |
| TDI 80 | 19.5 | 19.5 | 19.5 |
| TDI 65 | 19.5 | 19.5 | 19.5 |
| Isocyanate index | 106 | 106 | 106 |
| Additive according to Example 8 | 1.5 | — | — |
| Additive according to Example 7 | — | 1.0 | — |
| Additive according to Example 9 | — | — | 1.5 |
| Physical properties | | | |
| Density (kg/cm³) | 34 | 35 | 35 |
| Tensile strength (kPa) | 110 | 70 | 80 |
| Elongation at break (%) | 400 | 200 | 360 |
| Compression resistance at 40% (kPa) | 1.9 | 1.5 | 2.0 |
| Pressure deformation residue at 90% (%) | tacky | tacky | 88 |
| Welding time foam/foam (sec) | 3 | 5 | 2.5 |

The foams obtained according to Examples 19–29, from Tables 2 and 3, are also open-celled, free from faults and may easily be laminated to surface layers in the form of textiles or foils by high frequency welding. The welding seams obtained are clearly marked and the foam has fused to a thin film. No burn marks are formed and the welding seams cannot be separated without the foam tearing at the sides of the seam.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of polyurethane foams suitable for high frequency welding by the reaction of relatively high molecular weight compounds having molecular weights of from 400 to 10,000 and containing at least two isocyanate-reactive hydrogen atoms with polyisocyanates in the presence of catalysts and blowing agents, characterized in that ammonium salts of phosphorus-containing acids are added to the reaction mixture in an amount of from 0.1 to 10% by weight based on the total weight of the reaction mixture, said phosphorus-containing acids being selected from the group consisting of monoalkylphosphoric acids, dialkylphosphoric acids, dialkylphosphinic acids, monoalkylphosphonic acids, and monoalkylesters of monoalkylphosphonic acids.

2. The process of claim 1 wherein said salts correspond to the formula

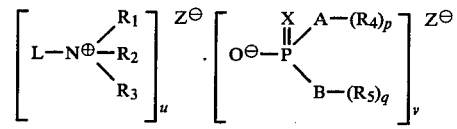

wherein

L represents hydrogen and/or a $C_1$ to $C_6$ alkyl;

$R_1$, $R_2$, and $R_3$ are the same or different and represent a member selected from the group consisting of:
  (i) hydrogen,
  (ii) linear or branched chain hydroxyalkylene groups with up to 10 C-atoms,
  (iii) linear or branched chain alkyl and cycloalkyl groups with up to 10 C-atoms, which may contain —O— or —N—alkyl-groups,
  (iv)

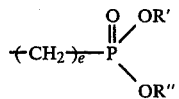

where R' and R" are the same or different and represent a $C_1$ to $C_{10}$ alkyl or hydroxyalkyl, (v)

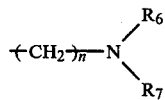

where $R_6$ and $R_7$ are the same or different and represent a linear or branched $C_1$ to $C_6$ alkyl (preferably methyl or ethyl), (vi)

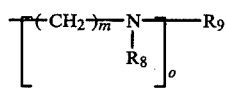

where $R_8$ and $R_9$ are the same or different and represent a linear or branched $C_1$ to $C_6$ alkyl (preferably methyl or ethyl), (vii)

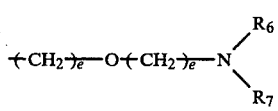

where $R_6$ and $R_7$ are as defined above, and (viii)

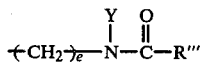

where R''' represents hydrogen or a $C_1$ to $C_6$ alkyl, and where Y represents any one of the radicals noted under (i) through (vii) above; and further wherein e represents an integer of from 1 to 10, n represents an integer of from 2 to 10, m represents an integer of from 2 to 10, o represents an integer of from 2 to 6, $Z^{\oplus}$ is the charge number of the cation, may be equal to or less than the total number of nitrogen atoms and is preferably 1 or 2, and u denotes the number of cations (preferably one or two) that may be present depending on the charge number $Z^{\oplus}$, such that $uZ^{\oplus} = vZ^{\ominus}$ (it is preferable that $uZ^{\oplus}$ equal one or two);

X represents an oxygen or sulfur atom;

A and B are the same or different and represent a member selected from the group consisting of (i) —$CH_2$—

(ii) an oxygen or sulfur atom, and (iii) an oxygen ($O^{\ominus}$) or sulfur ($S^{\ominus}$) ion;

p and q are either 0 or 1, and when A and/or B represents an oxygen or sulfur ion, the corresponding p or q must be zero;

$Z^{\ominus}$ is the charge number of the anion;

v represents the number of anions present, being an integer of 1 to 3 (preferably 1 to 2), such that $vZ^{\ominus} = uZ^{\oplus}$;

and $R_4$ and $R_5$ may be the same or different and represent hydrogen or a $C_1$ to $C_{10}$ alkyl or cycloalkyl.

3. The process of claim 2 characterized in that the ammonium salts of phosphorus-containing acids are dissolved in the relatively high molecular weight compounds containing at least two isocyanate-reactive hydrogen atoms.

4. The process of claim 2 characterized in that the ammonium salts of phosphorus-containing acids are dissolved in the polyisocyanates.

5. The process of claim 2 characterized in that ammonium salts of dibutyl phosphoric acid are used.

6. The process of claim 2 characterized in that ammonium salts of phosphonic or phosphinic acids are used.

7. The process of claim 2 characterized in that the reaction mixture also includes chain-lengthening agents having molecular weights of from 32 to 399, foam stabilizers and other auxiliary agents and additives.

8. The polyurethane foams produced in accordance with claim 1.

9. The polyurethane foams produced in accordance with claim 2.

* * * * *